(12) United States Patent
Yunus

(10) Patent No.: US 11,076,996 B2
(45) Date of Patent: Aug. 3, 2021

(54) BANDAGES FOR SUPPLYING OZONE THERAPY

(71) Applicant: Umm-Al-Qura University, Makkah (SA)

(72) Inventor: Mohammed Yunus, Bangalore (IN)

(73) Assignee: Umm-Al-Qura University, Makkah (SA)

( * ) Notice: Subject to any disclaimer, the term of this patent is extended or adjusted under 35 U.S.C. 154(b) by 354 days.

(21) Appl. No.: 15/169,538

(22) Filed: May 31, 2016

(65) Prior Publication Data
US 2017/0340870 A1 Nov. 30, 2017

(51) Int. Cl.
*A61F 13/00* (2006.01)
*A61M 13/00* (2006.01)
*A61M 37/00* (2006.01)
*A61M 35/00* (2006.01)

(52) U.S. Cl.
CPC .. *A61F 13/00029* (2013.01); *A61F 13/00063* (2013.01); *A61M 13/003* (2013.01); *A61M 35/30* (2019.05); *A61M 37/0015* (2013.01); *A61F 2013/0017* (2013.01); *A61F 2013/00285* (2013.01); *A61F 2013/00289* (2013.01); *A61M 2037/0023* (2013.01); *A61M 2202/0216* (2013.01)

(58) Field of Classification Search
CPC ...... A61M 35/30; A61M 37/0015–2037/0046; A61M 2037/0061; A61M 2202/0216; A61M 13/003; A61M 2037/0023; A61F 13/00029; A61F 13/00063; A61F 2013/0017; A61F 2013/00285; A61F 2013/00289; A61K 9/7084; A61K 9/7092
See application file for complete search history.

(56) References Cited

U.S. PATENT DOCUMENTS

| | | | |
|---|---|---|---|
| 2013/0018279 A1* | 1/2013 | Plante | A61B 5/150984 600/583 |
| 2013/0171722 A1* | 7/2013 | Chen | C12M 35/00 435/283.1 |
| 2013/0345650 A1* | 12/2013 | Amirouche | A61B 5/04001 604/305 |
| 2016/0256638 A1* | 9/2016 | Sarangapani | A61M 39/22 |

* cited by examiner

*Primary Examiner* — Theodore J Stigell
*Assistant Examiner* — Daniel Moore
(74) *Attorney, Agent, or Firm* — Geeta Kadambi; Riddhi IP LLC

(57) ABSTRACT

The present disclosure relates to a bandage wherein the bandage comprise of a first layer of protective covering, wherein the first layer is removable; a second layer of covering, wherein the second layer of covering is made of a cloth material; a third layer of covering, wherein the third layer is the top most layer of the bandage and together with the second layer forms a support pad; an injector, wherein the injector is present on the second layer of covering; a cylinder, wherein the cylinder is present in the support pad, wherein the bandage is used for delivering a medication to a localized area on a patient's body. The bandage is further used for delivering localized, painless ozone gas treatment to a patient suffering from infectious disease. The bandage is easy to carry and comes in various shapes and sizes.

9 Claims, 3 Drawing Sheets

BANDAGES FOR SUPPLYING OZONE THERAPY

FIELD OF TECHNOLOGY

This disclosure relates generally to a bandage for ozone therapy. Further, the present disclosure relates to a bandage for ozone therapy, wherein the bandage comprise of a nano-sized injector.

BACKGROUND

Bandages are often found in any first aid kit and used as first choice of treatment for keeping any medicine in place. There are different types of bandages available today, each for a different use. Different number of bandages available includes elastic bandages, adhesive zinc-oxide bandages, gauze pads, triangular bandages, suspensory bandages, roller bandages, four tailed bandages, compression bandages and tube bandages. all these bandages function by holding the injury, secure a dressing or provide a localized treatment for a limited amount of time.

There is a need to have a bandage that can aid in a treatment of a patient apart from just providing supporting functions.

SUMMARY

The present disclosure relates to an apparatus and a method of using the apparatus for a painless blood treatment of a patient. The apparatus as disclosed is a bandage and a method of using the bandage wherein the bandage is used for delivering a medication to a localized area on a patient's body for treatment.

In one embodiment, the present disclosure relates to a bandage wherein the bandage is made up of more than one layer. In another embodiment, the bandage further comprise of an injector for delivery of a medicine.

In one embodiment, the present disclosure relates to a bandage with a nano-sized injector wherein the injector supplies a desired medicine to a patient. In another embodiment, the bandage comprise of more than one nano-sized injector wherein the injector supply an ozone gas for providing a treatment to a patient.

In one embodiment, the bandage comprise of three layers such as a first layer, a second layer and a third layer whereas in another embodiment, the bandage comprise of an injector in between the first layer and the second layer. In yet another embodiment, the bandage further comprise of a cylinder present in between the second layer and the third layer.

In one embodiment, the first layer of covering is the outermost covering of the bandage which covers the tip of an injector present on the second layer of the covering. In another embodiment, the first layer of protective covering is a removable layer which needs to be removed very carefully before the use of the bandage. The first layer of protection may be made of a material which can withhold pressure from the injector tip and maintain its shape. The first layer of covering is present on the bandage when the bandage is not in use and the covering can be easily removed from the bandage by pulling it away from the bandage in a careful manner.

In one embodiment, the second layer of covering comprise an injector which is a nano-sized injector. In another embodiment, the second layer of covering of the bandage is the same layer which is placed in close contact with the skin area to be treated in a patient. Thus, the bandage makes contact with the skin of a patient through the second layer of covering. In yet another embodiment, the second layer also comprise of a sticky material on all the four sides of the bandage so that the bandage can stick onto the skin of the area to be treated when the bandage is to be used.

In one embodiment, the third layer of covering is the top most layer of the bandage whereas in another embodiment, the third layer is the one which is not in contact with the skin area to be treated in a patient. The second layer and third layer are assembled in a way as to form a support pad which also house a cylinder.

In one embodiment, the bandage as disclosed comprise of a first protective layer, an injector, a second layer, a cylinder and a third layer, wherein the bandage is used for delivering a medication to a localized area on a patient's body. In another embodiment, the present disclosure relates to a bandage wherein the bandage comprise of a first layer of protective covering; a second layer of covering, wherein the second layer of covering is made of a cloth material; a third layer of covering, wherein the third layer is the top most layer of the bandage; an injector, wherein the injector is present on the second layer of covering; a cylinder, wherein the cylinder is present in between second layer and third layer of covering, wherein the bandage is used for delivering a medication to a localized area on a patient's body. In yet another embodiment, the present disclosure relates to a bandage wherein the bandage comprise of a first layer of protective covering; a second layer of covering; a third layer of covering, wherein the third layer is the top most layer of the bandage and together with second layer forms a support pad; a nano-sized injector, wherein more than one injector is present on the second layer; a cylinder, wherein the cylinder is present in between the support pad and delivers an ozone gas, wherein the bandage is used for delivering ozone gas for treatment of an infectious disease.

The injector is a nano-sized injector and is present on the second layer of covering and thus makes contact with the area to be treated through the second layer of bandage. The injector may be spread over the whole surface area of the second layer of bandage or support pad or may be spread at one particular location over the surface area of the second layer of covering or support pad. The nano-sized injector may be prepared from a material known in the art and is unbreakable. The bandage makes contact with the skin of a patient and thus the area to be treated through the second layer of covering.

In one embodiment, the bandage is prepared from a generic cloth material whereas in another embodiment, this may be prepared from other know material such as composites. The material to be used should be soft, strong, flexible and non-tearable.

In one embodiment, the cylinder is embedded in a support pad, wherein the support pad is formed by an assembly of second layer and third layer of covering while in another embodiment, the cylinder is placed in the bandage such that it covers only sides of the bandage in between the two coverings. The cylinder may be made of plastic or of a known cushion material which is safe to be used with a medicine or ozone gas.

In one embodiment, the cylinder comprises of a body and a nozzle attached to the body. In another embodiment, the nozzle may be used for connecting to a refill containing a medicine to be delivered to a patient. A refill comprise of a body and a nozzle of the refill. The size of the nozzle of the refill is such that it fits into the nozzle of the cylinder. The refill comprise of the medication to be delivered to a patient. The medication can be in liquid form or in gaseous form such as ozone gas. Thus, in yet another embodiment, the nozzle may be connected to a refill comprising ozone gas supply such that the ozone gas can be supplied to an area of treatment via the bandage.

In one embodiment, a knob is also present on the nozzle of the cylinder to open or close the nozzle whereas in another embodiment, the knob helps in monitoring the amount to medication to be delivered through the bandage. The knob helps in providing a continuous flow of medication to the person for treatment. The knob is present on the outside of the nozzle and can be operated manually or electronically.

In one embodiment, the bandage can be used to supply any liquid medication or a gaseous medication to a person at a particular location on the body of the person wherein the bandage covers a particular area on the body to be treated. In another embodiment, the bandage can be made of varying shapes and sizes depending on the area to be treated.

In one embodiment, a method of using a bandage is disclosed wherein the method comprises: locating an area to be treated; cleaning and drying the area before applying the bandage; placing the bandage over the area; attaching a refill to a nozzle present on the bandage; switching a knob ON present on the nozzle of the bandage to release supply of a medication from the refill; applying a finger pressure over the top of the bandage to inject medication from the bandage into the area to be treated; repeating the finger pressure as required to release more medication; and switching OFF the knob present on the nozzle to stop release of medication from refill when the required amount of medication is released. In another embodiment, a method of using a bandage is disclosed, wherein the method comprises: locating an area on a patient's body to be treated; cleaning and drying the area before applying the bandage; removing a first layer of covering on the bandage; placing the bandage over the area; putting finger pressure on a side of the bandage to stick the bandage onto the area; attaching a refill to a nozzle present on the bandage; switching a knob ON present on the nozzle of the bandage to release supply of a medication from the refill; applying a finger pressure over the top of the bandage to inject medication from the bandage into the area to be treated through an injector, wherein a nano-sized injector is present in the bandage; repeating the finger pressure as required to release more medication; and switching OFF the knob present on the nozzle to stop release of medication from refill when the required amount of medication is released.

In yet another embodiment, a method of injecting ozone gas into blood through a bandage is disclosed, wherein the method comprises: locating an area on a patient's body to be treated; cleaning and drying the area before applying the bandage; removing a first layer of covering on the bandage; placing the bandage over the area; putting a finger pressure on a side of the bandage to stick the bandage onto the area; attaching a refill to a nozzle present on the bandage, wherein the refill comprises a supply of an ozone gas; switching a knob ON present on the nozzle of the bandage to release supply of ozone gas from the refill; applying the finger pressure over the top of the bandage to inject ozone gas from the bandage into the area to be treated through an injector, wherein a nano-sized injector is present in the bandage; repeating the finger pressure as required to release more ozone gas as required; and switching OFF the knob present on the nozzle to stop release of ozone gas from refill.

In one embodiment, the ozone gas as supplied through the bandage can help in treatment of infectious diseases such as diseases from virus, bacteria, fungi and protozoa in blood. In another embodiment, the use of ozone gas through the bandage can help a patient suffering from infectious disease without adversely affecting normal physiological activity, without pain or damage to blood cells. The bandage is used at a particular location and thus a localized treatment is provided.

The bandage as disclosed may be disposed off with a standard procedure as adopted for other surgical instruments. The bandage helps in directly injecting ozone gas at one particular place on the patient's body. Other features will be apparent from the accompanying drawings and from the detailed description that follows.

BRIEF DESCRIPTION OF DRAWINGS

Example embodiments are illustrated by way of example and not limitation in the figures of the accompanying drawings, in which like references indicate similar elements and in which.

Other features of the present embodiments will be apparent from the accompanying detailed description that follows.

DETAILED DESCRIPTION

The present invention to provide a bandage with nano sized injectors like apparatus and method for using the apparatus for supplying ozone gas for treatment of blood, wherein precise control is maintained over the concentration of ozone, so that infectious organisms are destroyed while normal biological and metabolic activities in the blood and blood products are not adversely affected.

Generally, Ozone is formed by splitting an oxygen molecule using an electric spark or ultra-violet (UV) light and it is triatomic allotrope of oxygen. Ozone is one of the most powerful natural oxidizing agents known because of the highly reactive free radicals generated on decomposition and thus they destroy many natural biological substances. Regardless of how the disease is transmitted, people are becoming infected at an alarming rate and an effective treatment is needed. Ozone is a potential oxidant that has been shown to possess broad spectrum antimicrobial activity. Advancements made by scientists in recent years using ozone to inactivate viruses, bacteria, fungi and protozoa have been well documented. Its effects are proven, consistent, and safe with minimal and preventable side effects. Injecting ozone into the blood is very painful method since it is injected either directly into the blood through syringe or ozonized water is sent in the form of drips or by an apparatus where blood is sent in it and mixed with ozone using counter flow.

Figure 1:
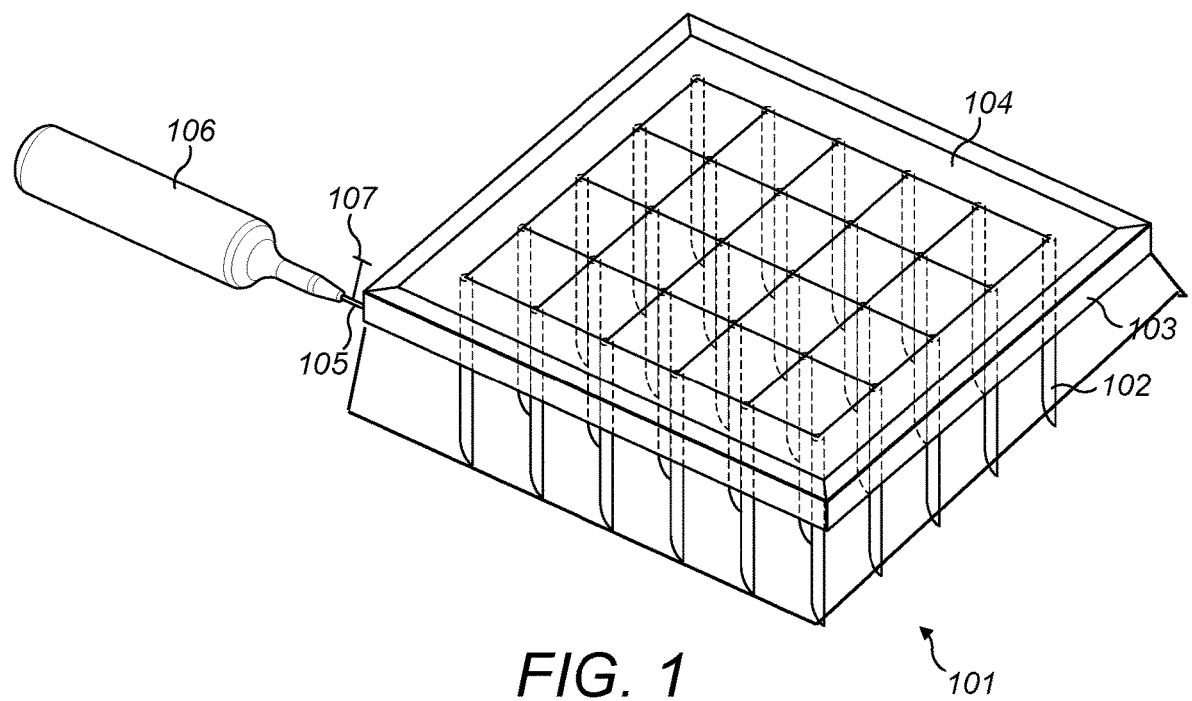
FIG. 1 shows an isometric view of a bandage.

FIG. 1 shows an isometric view of a bandage. As shown in FIG. 1, a bandage 101 as disclosed in the present application comprises of a nano-sized injector 102; a cylinder 103 present in a support pad 104. The bandage 101 further comprise of a nozzle 105 which is the opening of the cylinder 103. The nozzle is further connected to a refill 106, wherein the refill further comprise of a knob 107. The bandage comprise of more than one nano-sized injector 102. The injector may be spread on the whole surface area of the bandage (as shown in FIG. 1) leaving sides of the bandage or may be just localized to one particular location on the bandage. The bandage can be of varying sizes and shapes depending on a user's choice and area to be treated such as bandage for knee, arm, neck or others.

The bandage may be prepared from a generic cloth material or other known material such as composites. The material to be used should be soft, strong, flexible and non-tearable.

Figure 2:
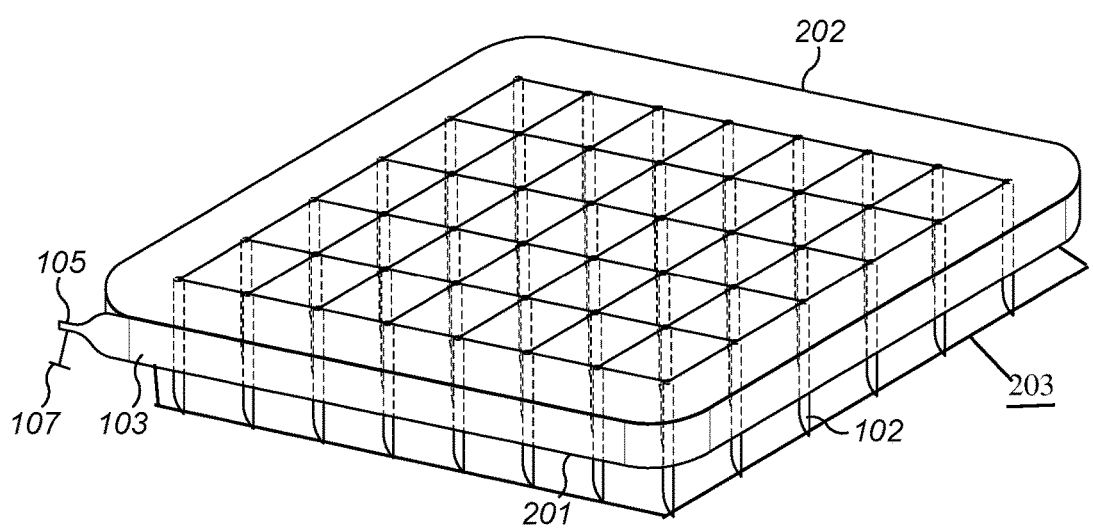
FIG. 2 shows details of cylinder present inside the bandage.

The cylinder 103 is embedded in a support pad 104, wherein the support pad is formed by an assembly of second layer 201 and third layer of covering 202 (as shown in FIG. 2). The cylinder may also be placed in the bandage such that it covers only sides of the bandage in between the two coverings. The cylinder may be made of plastic or of a known cushion and safe material that can be used to deliver medication or ozone gas. The cylinder comprise of a body 103 and a nozzle 105 attached to the body. The nozzle may be used for connecting to a refill 106 containing a medication to be delivered to a patient. Further, the nozzle may also be connected to a refill comprising ozone gas supply such that the ozone gas can be supplied to an area of treatment via the bandage. A knob 107 is also present on the nozzle 105 of the cylinder to open or close the nozzle and help in monitoring the amount to medication to be delivered through the bandage. The knob helps in providing a continuous flow of medication to the person for treatment. The knob is present on the outside of the nozzle and can be operated manually or electronically.

Figure 4:
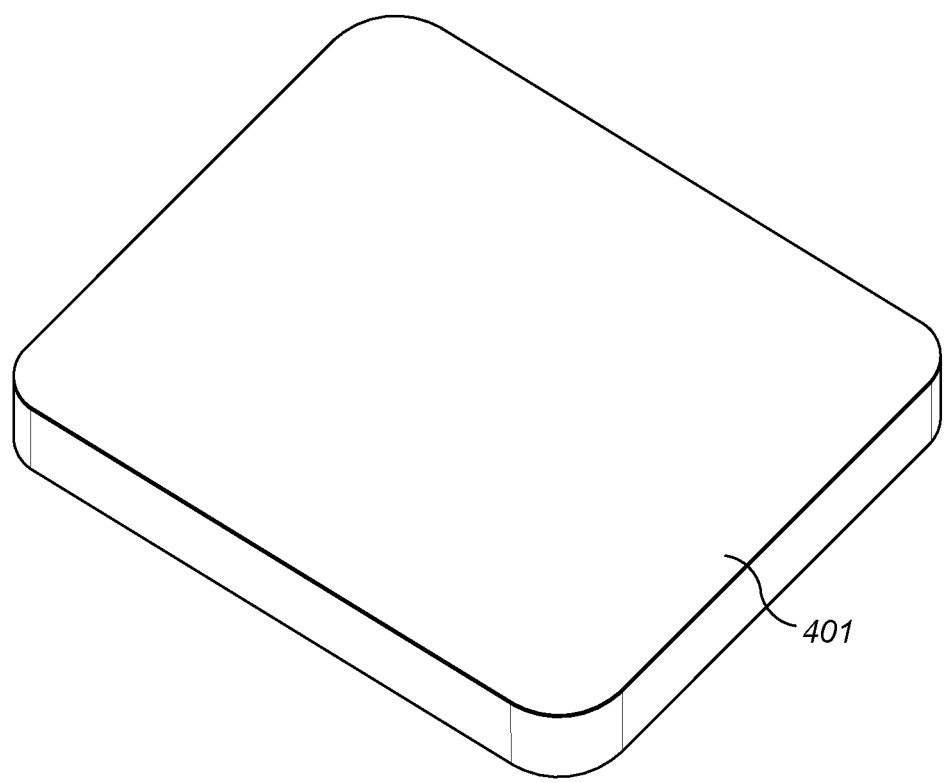
FIG. 4 shows another view of the bandage.

As shown in FIG. 2, the disclosed bandage comprise of three layers such as a first layer 203, a second layer 201 and a third layer 202 with an injector 102 in between the first layer 204 and the second layer 201. The bandage further comprise of a cylinder 103 present in a support pad 401 formed by the second layer and the third layer (as shown in FIG. 4). The first layer of covering is the outermost covering of the bandage which covers the tip of an injector present on the second layer of the covering. The first layer of protective covering is a removable layer which needs to be removed very carefully before the use of the bandage. The first layer of protection may be made of a material which can withhold pressure from the injector tip and maintain its shape and helps keeping the bandage in place. The first layer of covering is present on the bandage when the bandage is not in use and the covering can be easily removed from the bandage by pulling it away from the bandage in a careful manner.

The second layer of covering 201 comprises a nano-sized injector 102. The second layer of covering of the bandage is the same layer which is placed in close contact with the skin area to be treated in a patient. Thus, the bandage makes contact with the skin of a patient through the second layer of covering. The second layer also comprise of a sticky material on all the four sides of the bandage so that the bandage can stick onto the skin of the area to be treated when the bandage is to be used.

The third layer of covering 202 is the top most layer of the bandage and is the one which is not in contact with the skin area to be treated in a patient. The second layer and third layer are assembled in such a way as to form a support pad 104 which also house a cylinder 103.

Figure 3:
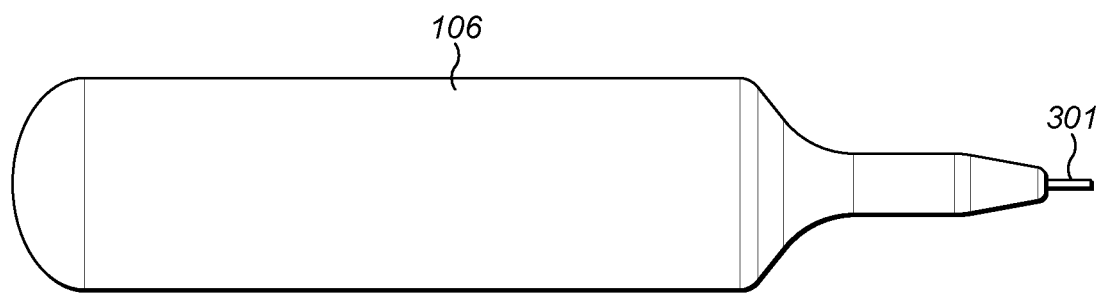
FIG. 3 shows details of a refill that can be attached to a nozzle on the cylinder.

As shown in FIG. 3, the refill 106 comprise of a body and a nozzle of the refill 301. The size of the nozzle of the refill 301 is such that it fits into the nozzle 105 of the cylinder 103. The refill comprise of the medication to be delivered to a patient. The medication can be in liquid form or in gaseous form such as ozone gas. There can be different sizes but with a nozzle of the refill of a size such that it can fit into the nozzle of the cylinder for its use.

The bandage can be used to supply any liquid medication or a gaseous medication to a person at a particular location on the body of the person wherein the bandage covers a particular area on the body to be treated. The bandage can be made of varying shapes and sizes depending on the area to be treated.

Figure 5:
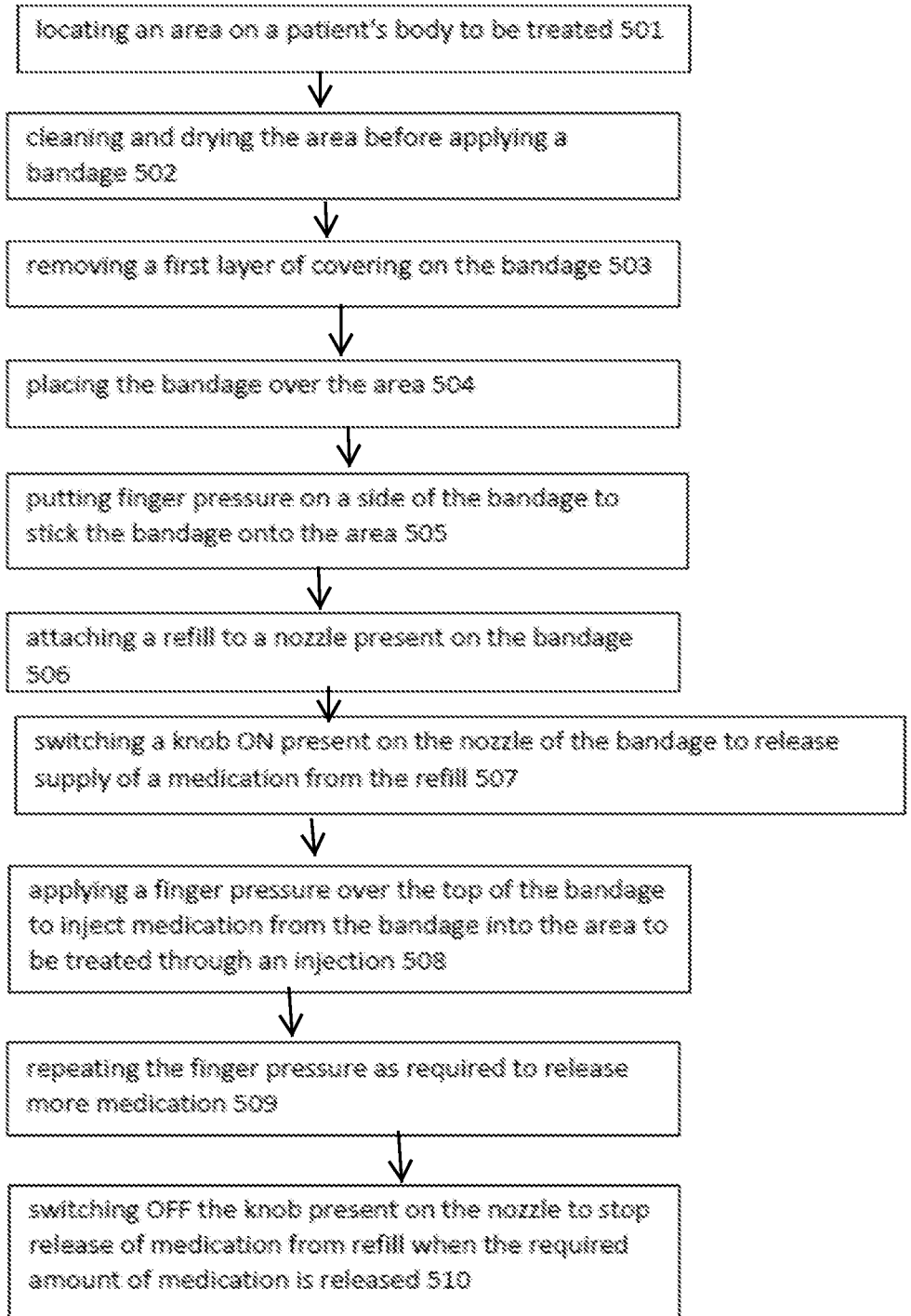
FIG. 5 shows steps of using the bandage.

Further, as shown in FIG. 5, the present disclosure also relates to a method of using a bandage, wherein the method comprises: locating an area on a patient's body to be treated 501; cleaning and drying the area before applying a bandage 502; removing a first layer of covering on the bandage 503; placing the bandage over the area 504; putting finger pressure on a side of the bandage to stick the bandage onto the area 505; attaching a refill to a nozzle present on the bandage 506; switching a knob ON present on the nozzle of the bandage to release supply of a medication from the refill 507; applying a finger pressure over the top of the bandage to inject medication from the bandage into the area to be treated through an injection 508, wherein a nano-sized injector is present in the bandage; repeating the finger pressure as required to release more medication 509; and switching OFF the knob present on the nozzle to stop release of medication from refill when the required amount of medication is released 510.

Also, the method is disclosed comprising: locating an area on a patient's body to be treated; cleaning and drying the area before applying the bandage; removing a first layer of covering on the bandage; placing the bandage over the area; putting finger pressure on a side of the bandage to stick the bandage onto the area; attaching a refill to a nozzle present on the bandage, wherein the refill comprises a supply of an ozone gas; switching a knob ON present on the nozzle of the bandage to release supply of ozone gas from the refill; applying a finger pressure over the top of the bandage to inject ozone gas from the bandage into the area to be treated through a cylinder, wherein a nano-sized injector is present in the bandage; repeating the finger pressure as required to release more ozone gas as required; and switching OFF the knob present on the nozzle to stop release of ozone gas from refill.

The present invention thus aims to provide a bandage for all group of patients (including teenagers, young and old group, sports personnel, etc.) especially, which considers general, emergency, safety, painless and protection requirements, to improvise upon the effect of the existing bandage/injecting method, thus makes quick and painless method, first aid effects conveniently and effectively for the different groups of people especially for their day to day life medication and various diseases.

The present invention is for injecting ozone in a very small level to large quantity supplied to any part or joint of the body to provide painless method, easily carriable, disposable and cost effective. The aim of the present invention is also to provide a simple bandage for ozone-therapy blood treatment, the technical characteristics of which are such as to overcome in a simple and inexpensive way the problems of the known art.

Due to the nano-size of needle of injectors to feed the ozone into the blood. It becomes painless to use on any part of the body. Further, many diseases cured by ozone gas can directly be injected at place where local effect can be increased for quick effect. The bandage is easy to carry in small quantity and change into required quantity by connecting with different sized refills. The bandage is easy to use and apply at any part of the body with minimum preparation without first aid facility.

This invention provide precise control of the concentration of ozone and the contact time between the blood and the ozone-oxygen mixture. The invention is described herein as applied to the treatment of infectious diseases in humans and principles are equally applicable to animals. Further, the invention also provides means for controlling proportionately ozone concentration at blood flow rate.

Although the present embodiments have been described with reference to specific example embodiments, it will be evident that various modifications and changes may be made to these embodiments without departing from the broader spirit and scope of the various embodiments.

What is claimed is:

1. A bandage, consisting of:
   a first layer (203) of protective covering located as an outer most layer for the bandage and covers one or more nano-sized injectors, wherein the first layer of protective covering is made of a material which can withhold pressure from a tip of the one or more nano-sized injectors (102) and maintains the shape of the one or more nano-sized injectors;
   a second layer (201) of covering consists of the one or more nano-sized injectors and a sticky outer layer, wherein the second layer of covering is made of a cloth material;
   a third layer (202) of covering, wherein the third layer is the top most layer of the bandage and does not come in contact with the skin;
   a cylinder (103) consists of a body and a nozzle (105) wherein the cylinder lays between the second layer and the third layer and covers all four sides of the bandage, wherein the nozzle contains a knob to meter the a medication into the cylinder, wherein the bandage is used for delivering a medication to a localized area on a patient's body; and
   a refill (106) contains the medication and delivers the medication by attaching itself to the nozzle of the cylinder.

2. The bandage of claim 1, wherein the first layer of protective covering is removable when the bandage is used.

3. The bandage of claim 1, wherein the one or more nano-sized injectors is present on the second layer of covering.

4. The bandage of claim 1, wherein the second layer and third layer are assembled in such a way as to form a support pad.

5. The bandage of claim 4, wherein the cylinder is embedded in the support pad.

6. The bandage of claim 1, wherein the medication is an ozone gas, wherein the bandage is configured to provide a continuous and painless ozone gas treatment delivered through the one or more nano-sized injectors to the patient.

7. The bandage of claim 1, wherein the bandage is used to deliver an ozone gas for the treatment of an infectious disease.

8. The bandage of claim 1, wherein the cylinder is connected to the refill and by switching the knob present on the nozzle of the bandage to an ON position enables the release the supply of the medication from the refill.

9. The bandage of claim 8, wherein the medication is a liquid medication to be delivered to the patient's body.

* * * * *